United States Patent
Nagale et al.

(10) Patent No.: US 10,695,128 B2
(45) Date of Patent: Jun. 30, 2020

(54) METHODS AND DEVICES FOR TARGETED ABLATION OF TISSUE

(71) Applicant: Boston Scientific Scimed, Inc., Maple Grove, MN (US)

(72) Inventors: Sandra Nagale, Bolton, MA (US); Michael C. Larson, Colorado Springs, CO (US); Mark Boden, Harrisville, RI (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 233 days.

(21) Appl. No.: 15/130,644

(22) Filed: Apr. 15, 2016

(65) Prior Publication Data

US 2016/0302868 A1    Oct. 20, 2016

Related U.S. Application Data

(60) Provisional application No. 62/148,525, filed on Apr. 16, 2015.

(51) Int. Cl.
*A61B 18/22* (2006.01)
*A61B 18/24* (2006.01)
*A61B 18/00* (2006.01)
*A61B 18/20* (2006.01)

(52) U.S. Cl.
CPC .............. *A61B 18/22* (2013.01); *A61B 18/24* (2013.01); *A61B 2018/00517* (2013.01); *A61B 2018/00577* (2013.01); *A61B 2018/2005* (2013.01); *A61B 2018/2238* (2013.01); *A61B 2018/2255* (2013.01); *A61B 2018/2272* (2013.01)

(58) Field of Classification Search
CPC ............ A61B 18/18; A61B 2018/1807; A61B 2018/1861; A61B 2018/1869; A61B 18/20; A61B 2018/2005; A61B 2018/2015; A61B 2018/2035; A61B 18/22; A61B 2018/2205; A61B 2018/2244; A61B 2018/2255; A61B 2018/2261; A61B 2018/2272; A61B 18/24; A61B 18/245; A61B 18/26; A61B 18/263; A61B 18/00; A61B 2018/00315; A61B 2018/00404; A61B 2018/00505; A61B 2018/00517; A61B 2018/00571
USPC ........................ 606/2.5, 6, 7, 13–19; 128/898
See application file for complete search history.

(56) References Cited

U.S. PATENT DOCUMENTS

| | | | | |
|---|---|---|---|---|
| 4,566,438 A | * | 1/1986 | Liese | A61B 5/6848 600/129 |
| 5,253,312 A | * | 10/1993 | Payne | A61B 18/22 385/123 |
| 5,469,524 A | * | 11/1995 | Esch | A61B 1/015 385/117 |
| 5,855,577 A | * | 1/1999 | Murphy-Chutorian | A61B 18/24 606/15 |

(Continued)

*Primary Examiner* — Ahmed M Farah
(74) *Attorney, Agent, or Firm* — Bookoff McAndrews, PLLC

(57) ABSTRACT

In one aspect, the present disclosure is directed to a system and method for ablating tissue. The method may comprise, for example, aligning a needle of a medical device with the target tissue; piercing tissue adjacent to the target tissue with the needle; sliding into the target tissue a laser fiber moveably disposed within the needle, wherein the needle is hollow and the laser fiber includes a prism; and delivering laser energy through the laser fiber and prism.

12 Claims, 6 Drawing Sheets

(56) References Cited

U.S. PATENT DOCUMENTS

| | | | | | |
|---|---|---|---|---|---|
| RE36,473 | E | * | 12/1999 | Esch | A61B 1/018 |
| | | | | | 385/117 |
| 6,231,568 | B1 | * | 5/2001 | Loeb | A61B 18/24 |
| | | | | | 606/15 |
| 6,594,518 | B1 | * | 7/2003 | Benaron | A61B 5/0059 |
| | | | | | 600/342 |
| 2002/0151879 | A1 | * | 10/2002 | Loeb | A61B 18/22 |
| | | | | | 606/15 |
| 2003/0083607 | A1 | * | 5/2003 | Bobo, Jr. | A61B 18/24 |
| | | | | | 604/20 |
| 2003/0199860 | A1 | * | 10/2003 | Loeb | A61B 18/24 |
| | | | | | 606/17 |
| 2005/0131399 | A1 | * | 6/2005 | Loeb | A61B 18/24 |
| | | | | | 606/15 |
| 2005/0251116 | A1 | * | 11/2005 | Steinke | A61B 5/0066 |
| | | | | | 606/8 |
| 2015/0378186 | A1 | * | 12/2015 | Xiong | G02F 1/093 |
| | | | | | 359/484.04 |
| 2018/0110554 | A1 | * | 4/2018 | Zarins | A61B 17/42 |

\* cited by examiner

METHODS AND DEVICES FOR TARGETED ABLATION OF TISSUE

CROSS-REFERENCE TO RELATED APPLICATIONS

This patent application claims the benefit of priority under 35 U.S.C. § 119 to U.S. Provisional Patent Application No. 62/148,525, filed Apr. 16, 2015, which is herein incorporated by reference in its entirety.

FIELD OF THE DISCLOSURE

The disclosure relates generally to ablating tissue with laser energy, and, more specifically, to methods and associated systems for accessing and ablating tissue.

BACKGROUND

Overactive Bladder (or "OAB") is one of the factors that can result in urinary incontinence conditions. OAB is a chronic urological condition characterized broadly as the involuntary and uncontrollable urge felt by a subject to relieve the bladder, leading to abnormally high urinary frequency and urgency. Such conditions may occur due to frequent and spontaneous contractions of the detrusor muscle of the pelvic region of a subject.

In patients with OAB, the bladder wall exhibits localized changes including local pathological changes in the muscle (e.g. patchy denervation, increased amount of connective tissue between muscle bundles) which may contribute to abnormal function of the detrusor muscle on a macroscopic scale and could be detected and subsequently treated. Current solutions for overactive bladder treatment (e.g. systemic drugs, nerve stimulation, and Botox injections) target the abnormal function of the entire bladder and do not specifically address local and anatomical abnormalities, thereby indicating a need for devices capable of identifying and providing therapy to specific areas where local bladder abnormality originates. Further, current device based treatments like Botox injections need to be repeated as the effect wears off over time. Further, overtreatment with Botox leads to urinary retention which requires self-catheterization in order to void.

If a local origin of contractions is identified, this area may be treated. While providing a local treatment of the bladder wall, however, it is important to ensure that the mucosa (which acts as the barrier between urine and nerves/muscle) remains intact or only temporarily injured when treatment is administered. An ideal treatment affects the morphology of muscle and nerves whereas mucosa remains minimally affected by treatment modality.

Ablation is currently used in a variety of treatments to remove biological tissue via heating and may rectify some of the deficiencies of current solutions described above.

Ablation is used to treat other conditions, including, but not limited to ablating a portion of the epidermis and/or fat deposits below the skin to remove wrinkles and/or cellulite, brain tissue to treat Parkinson's disease and/or psychiatric disorders, tissue within the cornea to treat astigmatism, myopia, and hyperopia, and/or the uterine wall to treat menstruation issues and adenomysis. Ablation of tissue can also be used to remove unwanted cells like tumors and/or treat snoring. The area treated by current devices, however, is limited by the diameter of the laser; only tissue adjacent to the distalmost end of the laser fiber is heated. For treatment of OAB, as well as any other conditions tissue ablation treats, there exists a need for a device that can access and ablate a larger area of tissue without increasing the diameter of the laser fiber that penetrates the tissue. The systems and methods of the current disclosure address these deficiencies in the current art and/or other problems in the art.

SUMMARY

Aspects of the present disclosure provide systems and methods for targeting tissue for ablation.

It is to be understood that both the foregoing general description and the following detailed description are exemplary and explanatory only and are not restrictive.

In one example, a medical device may include at least one needle, a laser source, a laser fiber moveably disposed within the at least one needle and coupled to the laser source, and a tip portion at a distal end of the laser fiber may be configured to change a direction of travel for laser energy emitted by laser fiber.

Examples of the medical device may additionally and/or alternatively include one or more other features. For example, the tip portion may have a prism capable of dissipating the laser energy and the prism is attached to the distal end of the laser fiber. The prism may be a triangular prism and the angle of a face attached to the distal end of the laser fiber may be between approximately 15 degrees and 75 degrees relative to a longitudinal axis of the laser fiber. The tip portion may be a reflective surface of the laser fiber. The laser fiber may be longitudinally moveable and, when in an extended position, at least a portion of the prism is distal to the distal end of the needle. When the laser fiber is in a retracted position, a distalmost end of the prism may be proximal to a distalmost end of the needle.

In another example, a medical device may include a catheter including a proximal end, a distal end, and at least one lumen extending between the proximal end and the distal end, a hollow needle movable disposed within the at least one lumen of the catheter, a laser fiber moveably disposed within the hollow needle, a prism disposed at a distal end of the laser fiber, and a laser source attached to the laser fiber.

Examples of the medical device may additionally and/or alternatively include one or more other features. For example, the laser fiber may be rotatable within the needle. The prism may be a triangular prism and the angle of a face attached to the distal end of the laser fiber may be between approximately 15 degrees and 75 degrees relative to a longitudinal axis of each laser fiber. The medical device may include a plurality of needles. The target tissue may be within the urinary tract. The laser fiber may be longitudinally moveable. When the laser fiber is in an extended position, at least a portion of the prism may be distal to the distal end of the needle. When the laser fiber is in a retracted position, a distalmost end of the prism may be proximal to a distalmost end of the needle. The hollow needle may include an angled distal end.

In another example, a method for ablating target tissue may include aligning a needle of a medical device with the target tissue, piercing tissue adjacent to the target tissue with the needle, sliding into the target tissue a laser fiber moveably disposed within the needle, wherein the needle is hollow and the laser fiber includes a prism, and delivering laser energy through the laser fiber and prism.

Examples of the method may additionally and/or alternatively include one or more other features. For example, inserting a catheter into the patient, wherein the needle may be disposed within a lumen of the catheter. The target tissue may be within a bladder of the patient. The pierced tissue may be part of mucosa and the target tissue is part of submucosa. The method may include rotating the laser fiber. The method may include introducing at least one of a fluid or a gel into the target tissue through a space between the needle and the laser fiber. The method may include delivering laser energy through the laser fiber and the prism into the target tissue.

BRIEF DESCRIPTION OF THE DRAWINGS

The accompanying drawings, which are incorporated in and constitute a part of this specification, illustrate exemplary aspects of the present disclosure and together with the description, serve to explain principles of the disclosure.

DESCRIPTION OF EXEMPLARY EMBODIMENTS

The present disclosure relates generally to accessing and ablating target tissue. Specifically, the disclosure relates to ablating a larger area of target tissue by directing laser energy through a prism disposed on a distal end of a laser fiber. Tissue ablation is used to treat a variety of medical conditions, including, tumors, eye disorders, psychological disorders, skin conditions, digestive tract conditions, and urinary tract conditions. One such condition may be overactive bladder. A needle may be used to perforate the bladder mucosa to the depth of submucosa. A laser fiber may be used to deliver laser energy to nerve endings and detrusor. The laser fiber has a prism used to dissipate light to surrounding tissue so the ablation area is expanded while a narrow needle and fiber are used to perforate mucosa, thus minimizing the damage to the mucosa. Once ablation of nerves and detrusor is achieved, the needle with the laser fiber may be retracted.

The examples described in this disclosure focus on accessing and ablating tissue within the bladder wall to treat overactive bladder, but the system and methods described herein are not limited thereto. For example, the devices and methods described herein may be used in the gastrointestinal tract and/or or another lumen in the body where subsurface ablation while maintaining a substantially intact mucosa or outer surface is desired. In other examples, the needle assembly described with respect to FIGS. 1 and 3-5 may be used without a catheter and the needle may pierce a patient's skin and ablate target skin tissue to treat wrinkles and/or ablate fat to treat cellulite.

Reference is now made in detail to examples of the present disclosure, examples of which are illustrated in the accompanying drawings. Wherever possible, the same reference numbers will be used throughout the drawings to refer to the same or like parts. The term "distal" refers to a position farther away from a user end of the device. The term "proximal" refers a position closer to the user end of the device. As used herein, the term "approximately" indicates a range of values within +/−5% of a stated value.

Figure 1:
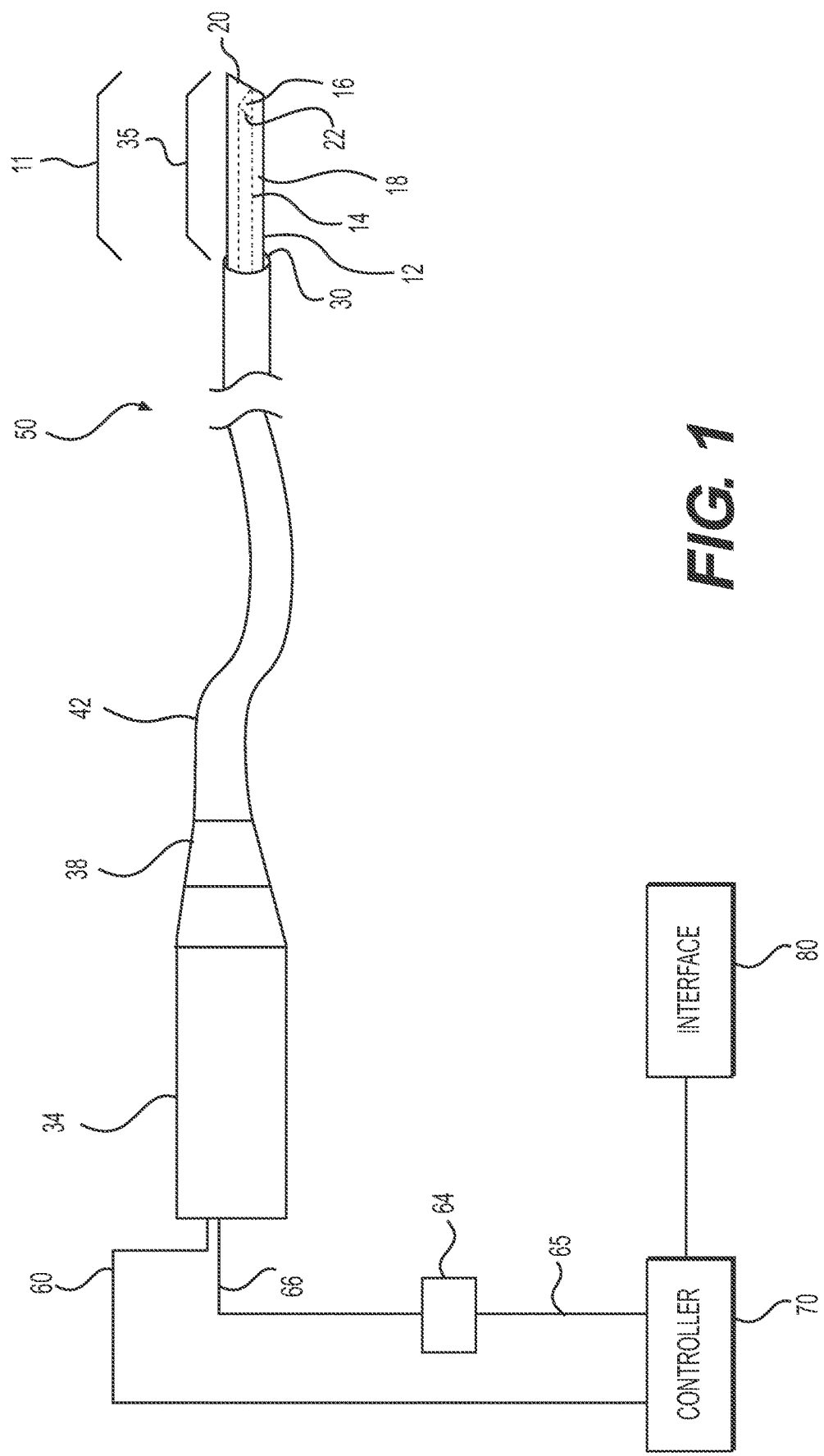
FIG. 1 illustrates a system for ablating target tissue in accordance with principles of the present disclosure.

FIG. 1 illustrates an exemplary medical device 50. Medical device 50 may include a catheter 42, a handle portion 34, and a needle assembly 11. Catheter 42 may have a proximal end 38 and a distal end 30. Handle portion 34 may be disposed at proximal end 38 of catheter 42. Handle portion 34 may include various positioning controls to allow for accurate positioning of the catheter 42, needle assembly 11, and/or laser assembly 35. These controls may allow an operator to steer catheter 42, needle assembly 11, and/or laser assembly 35. The controls may create longitudinal and/or rotational movement of needle assembly 11 relative to catheter 42 and/or laser assembly 35 relative to needle assembly 11. These movements may be controlled by a variety of controls, including, but not limited to, a slide block, a mechanical knob, an actuator, a motor, a computer program, input into an interface (e.g., interface 80), pull wires, etc. In some examples, these controls may be connected to a portion of the needle assembly 11 and/or laser assembly 35 that is within and/or connected to handle 34. In one example, a mechanical knob is coupled around an exterior of the laser assembly 35. Rotation of the mechanical knob may rotate the proximalmost end and/or the portion of the laser assembly disposed with handle 35 and this rotation of the proximalmost end may translate into the rotation of the whole laser assembly 35, including a distal end of laser assembly 35. In some examples, a combination of controls may be used. For example, the catheter 42 may be steered by pull wires, needle assembly 11 may be positioned using a slide block, and laser assembly 35 may be longitudinally moved by a slide block and rotated by a motor.

Catheter 42 may be a tube made from any suitable biocompatible material known to one of ordinary skilled in the art having sufficient flexibility to traverse a urinary tract. Such materials may include, but are not limited to, rubber, silicon, synthetic plastics, stainless steel, metal-polymer composites, and metal alloys of nickel, titanium, copper cobalt, vanadium, chromium, and iron. In one example, the material forming catheter 42 may be a superelastic material such as nitinol, which is a nickel-titanium alloy. Catheter 42 may have any cross-sectional shape and/or configuration and may be any desired dimension that can be received in the lower urinary tract. An outer sheath may surround catheter 42. Outer sheath may be constructed from an insulating polymer material such as polyamide, polyurethane, or any other suitable material. Catheter 42 may include one or more lumens extending from proximal end 38 of the catheter 42 to distal end 30 of the catheter 42. The lumens may have any size, cross-sectional area, shape, and/or configuration.

Needle assembly 11 may be longitudinally and/or rotatably moveably disposed within catheter 42. As shown in FIG. 1, needle assembly 11 can be moved longitudinally to extend beyond the distal end 30 of catheter 42. Needle assembly 11 may include needle 12 and a laser assembly 35.

Needle 12 may be any type, size, and/or design suitable for the desired target tissue and/or implementation. For example, needle 12 may be hollow and/or a semi-flexible metal needle. Needle 12 may include a sharp angled distal end 20. In some examples, the needle tip may be blunt with sharpened edges. Sharp angled distal end 20 may be used to pierce tissue in order to access target tissue. The needle 12 may be any diameter. In some examples, the outer diameter of the needle 12 may be small enough to move with a lumen of the catheter 42 (e.g., smaller than the diameter of the lumen). In some examples, the inner diameter of the needle 12 may be large enough to include the laser assembly 35. In some examples, the inner diameter of the needle 12 may be between approximately 0.05 mm and approximately 0.2 mm. In some examples, the inner diameter of needle 12 may be approximately 0.05 mm to approximately 1.5 mm; approximately 0.1 mm to approximately 1.0 mm, approximately 0.5 mm to approximately 1.0 mm, and/or may be less than approximately 0.1 mm.

In some examples, the needle may be pushed into the tissue and then slightly retracted (e.g., approximately 50 to approximately 150 microns, and/or approximately 100 microns). The retraction may provide space for the fiber to reach the target tissue. A mechanical stopper (not shown) may be used to fix the fiber at a position that reaches the target tissue. In another example, markers and/or slots (not shown) may be added to the handle and may secure the needle at different distances and/or secure the laser fiber/needle distance within the tissue.

The laser assembly 35 may include a laser fiber 14. Laser fiber 14 may include a tip portion having a prism 16, e.g. prism 16 may be disposed on a distal end 22 thereof. In some examples, prism 16 may be attached to the distal end 22 of laser fiber 14. Additionally or alternatively, prism 16 may be contained within/embedded in laser fiber 14, integrally formed within laser fiber 14, or comprise an altered section of laser fiber 14 capable of performing the functions described herein. In some examples, the prism and the laser fiber may be separated by an additional object.

Prism 16 may be any geometric shape. FIGS. 1 and 3-5 illustrate a triangular prism, but the disclosure it not limited thereto. Prism 16 may be any size or shape that accepts laser energy into a first face from the distal end 22 of laser fiber 14 and dissipates the laser energy out of a second face and into target tissue. In the examples shown in FIGS. 4 and 5, the angle between the first face and the second face is angle β. Angle β may be between approximately 15 degrees and 75 degrees. Angle β may be determined based on the desired exit angle of the laser energy, as known in the art. An angle of the distal end 22 of laser fiber 14 relative to a longitudinal axis of the laser fiber 14 and angle β may be supplementary angles. The first face of prism 16 may be attached to the distal end 22 of laser fiber 14 in any way, including but not limited to fusing the two together or applying adhesive between the two.

Laser fiber 14 may be any fiber capable of transmitting laser energy. For example, the laser fiber 14 may be single-mode or multi-mode. A multi-mode fiber may result in beam size that is focused to the desired diameter. The laser fiber 14 may be any diameter. The diameter of the laser fiber is smaller than the inner diameter of needle 12 to allow the laser fiber 14 to move within the needle 12. The laser fiber may be made of any material, including glass or polymer. In some examples, as an alternative to (or in addition to) the laser fiber 14, a radio frequency ablation, cryo ablation, and/or ultrasound catheter may be disposed within hollow needle 12 for treatment of the target tissue.

Space 18 may be disposed between needle 12 and laser fiber 14. The space 18 between needle 12 and laser fiber 14 may be any width. In some examples, the space 18 may be the minimum to allow movement of the laser fiber 14 within the needle 12. In some examples, the space 18 may be large enough to allow fluid and/or gel to pass between the laser fiber 14 and the needle 12. For example, fluid and/or gel may be used as a lubricant to facilitate fiber rotation without friction. The fluid and/or gel may be a polymer, polymer with pharmaceuticals, and/or a liquid/gel solution of pharmaceuticals. These pharmaceuticals may include, for example, neurotoxins, local anesthetics, antimuscarinics, anti-inflammatories, a beta adrenergic agonists, and/or other known drugs used to treat OAB, tissue inflammation, bladder cancer, and/or any other conditions the device is being used to treat. The liquid/gel may also contain fluorescent dyes or photosensitive dyes. For example, after a dye is injected, the laser light emitting from a distal end of laser fiber 14 may chemically alter the dye to destroy cells and/or ablate tissue (e.g., photodynamic therapy).

As noted above, the laser assembly 35 may be moveably disposed within hollow needle 12. In the retracted position of the laser assembly 35, the distalmost end of prism 16 may be proximal to the distal end 20 of hollow needle 12. The laser assembly 35 may be in the retracted position, for example, during insertion of the needle assembly 11 through catheter 42 and/or when the distal end 20 of hollow needle 12 pierces tissue. In an extended configuration, at least a portion of prism 16 (and, in some embodiments, a portion of laser fiber 14) may be distal to the distal end 20 of hollow needle 12. In the extended position, the prism 16 may extend any distance beyond the distal end 20 of hollow needle 12. For example, only a portion of the prism 16 may extend beyond the distal end 20 of hollow needle 12 or the entire prism 16 may be external to the hollow needle 12. In some examples, portions of the laser fiber 14 may extend distally out of the hollow needle 12 when the laser assembly 35 is in the extended position. The distance the prism 16 extends beyond the distal end 20 of the needle may depend on the implementation. For example, a larger target tissue area may be necessary for certain procedures, thus requiring the prism to extend further from the distal end 20 of needle 12 and/or require a larger prism. Further, depending on the laser assembly configuration, the prism 16 should extend far enough to avoid ablation of the interior wall of the needle 12. Additionally or alternatively, the needle 12 may pierce the tissue, laser fiber 14 may be introduced, and then needle 12 may be retracted, leaving laser fiber 14 in the tissue. This may minimize the length of time during which needle 12 is inserted in tissue.

In some examples, during insertion of the catheter into the patient and/or during alignment of the needle assembly 11 at a target tissue, a protective barrier (not shown) may prevent fluid from entering hollow needle 12 from the distal end 20. This protective barrier may be configured to allow the prism 16 to pass through the barrier when the laser assembly 35 is moved distally. For example, the protective barrier may be a one way flap/valve, or may be predisposed to rupture as a result of pressure from prism 16 or a sharp end of prism 16.

In some examples, laser fiber 14 and with it prism 16 may be rotated, thus allowing the light dissipating out of the second face of the prism 16 to be directed to the entire volume of tissue surrounding needle insertion site (e.g., the full 360 degrees). In some examples, a motor (not shown) or manual knob (not shown) may be used to rotate the laser assembly.

In one example, medical device 50 may attach to or include a controller 70 and an interface 80. Controller 70 may include signal processing, laser control, and/or an electrical energy source connected to handle 34 of medical device 50 via one or more wires 60 and/or to a laser source 64 via one or more wires 65, respectively. In some implementations, medical device 50 may include other components, including, but not limited to, a fluid source, a coolant source, and/or a vacuum source.

Laser source 64 may be any device or system that delivers laser energy. Various laser sources in the ultraviolet, visible, or infrared range may be used. A laser source in the infrared range may be preferred for tissue heating. Laser source 64 may be connected to handle 34 via laser fiber 66. Laser source 64 may be controlled by controller 70. Additionally or alternatively, controller 70 may control and/or allow an operator to control the operation of various components of medical device 50. In some implementations, controller 70 may control the steering of catheter 42 and/or needle assembly 11 and/or movement of laser fiber 14. In one example, controller 70 may control the frequency, pattern, and/or strength of laser energy delivered from the laser source 64 to laser fiber 14. Controller 70 may perform, in whole or in part, exemplary methods described in further detail with respect to method 200 of FIG. 2.

In some implementations, controller 70 may include, for example and without limitation, a processor, and memory for executing and storing processor-readable instructions. The memory may include any type of random access memory (RAM) or read-only memory (ROM) embodied in a physical storage medium, such as magnetic storage including floppy disk, hard disk, or magnetic tape; semiconductor storage such as solid state disk (SSD) or flash memory; optical disc storage; or magneto-optical disc storage. Software may include one or more applications and an operating system.

In some implementations, controller 70 may be connected to interface 80. The interface 80 may communicate to controller 70 input commands from an operator, including commands used to control and/or provide data to a laser source 64 and/or any other components of medical device 50. Interface 80 may include user input device(s), including but not limited to any type or combination of input/output devices, such as a display monitor, touchpad, touchscreen, microphone, camera, keyboard, and/or mouse. Interface 80 may include a display screen for output to an operator. Controller 70 may provide operator information to interface 80

Figure 2:
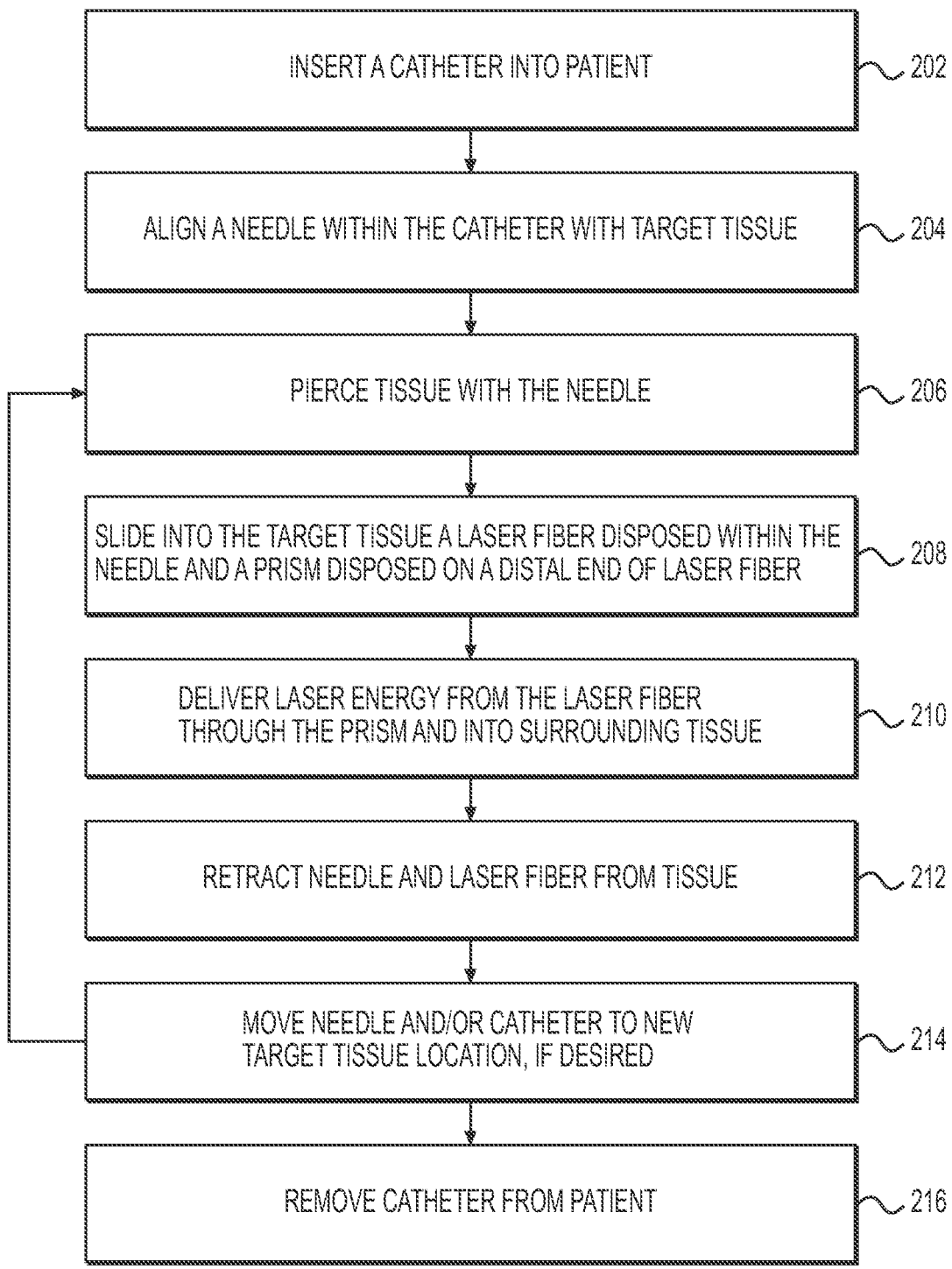
FIG. 2 is a block diagram of an exemplary method of applying laser energy to target tissue in accordance with principles of the present disclosure.

FIG. 2 is a process flow diagram of an exemplary method 200 for accessing and ablating target tissue within a patient. For purposes of discussion, method 200 will be described using medical device 50 of FIGS. 1 and 3, and urinary tract 300 of FIG. 3, but method 200 is not intended to be limited thereto. For example, in some implementations, the target tissue is in another area of the body (e.g., skin, eye, brain, digestive tract). As shown in FIG. 2, method 200 includes steps 202, 204, 206, 208, 210, 212, 214, and 216. However, it should be noted that method 200 may include more or fewer steps as desired for a particular implementation and the steps may be performed in any order. In an example, one or more of the above-listed steps of method 200 may be executed by an operator, medical device 50, controller 70, and/or interface 80 of FIG. 1, as described above. However, method 200 is not intended to be limited thereto, and the steps of method 200 may be performed by any party, module, device, and/or server.

Figure 3:
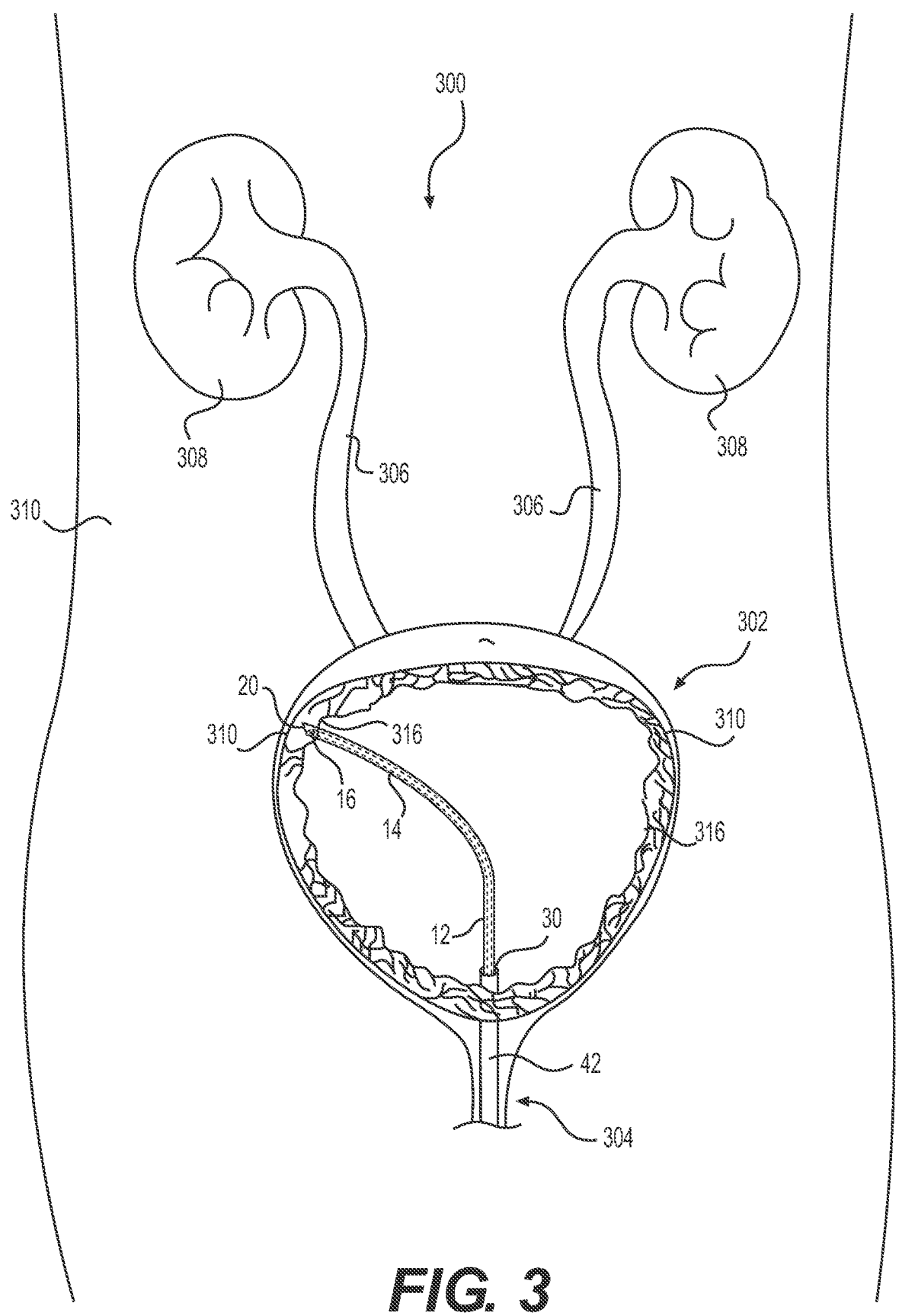
FIG. 3 is a schematic view of an exemplary ablation system within a patient in accordance with principles of the present disclosure.

Method 200 begins in step 202, which may include inserting a catheter into a patient. For example, FIG. 3 illustrates an exemplary schematic view of step 202, inserting catheter 42 into patient 310. FIG. 3 is a schematic view of an exemplary embodiment of the present disclosure, implemented for and in a urinary tract 300 of a patient 310. While this disclosure relates to the use of the disclosed system in the urinary tract of a human subject, as noted above, it is understood that the features of this disclosure could be used in other locations (other organs and tissue) within a patient.

The urinary tract 300 includes, among other structures, a bladder 302 that is in fluid communication with a urethra 304. Bodily fluid, such as urine, travels down from kidneys 308 to the bladder 302 via ureters 306. Muscles (not shown) in the walls of the ureters 306 tighten and relax to force the bodily fluid downward and away from the kidneys 308. The bladder 302 generally accumulates the bodily fluid, which is then discharged from the body through urethra 304. In some implementations, catheter 42 may be inserted into the body through the urethra 304 to bladder 302 and the needle assembly 11, shown in FIG. 3, may be disposed completely proximal to the distal end 30 of catheter 42 (not shown). For example, the needle assembly 11 may be located within a lumen of catheter 42 during insertion and then exit the distal end 30 of catheter 42 once at the desire location, e.g. within bladder 302 as shown in FIG. 3.

As previously mentioned, method 200 may include more or less steps. In an application in which the target tissue is below the skin (e.g., treatment for wrinkles or cellulite), method 200 may proceed directly to step 204, as a catheter is not needed to access the target tissue. Rather, the needle 14 will pierce the skin from exterior of the patient 310.

Once catheter 42 is introduced into the bladder 302 in step 202, method 200 may proceed to step 204. Step 204 may include aligning a needle within the catheter with the target tissue. For example, catheter 42 may be placed near the target tissue or, as shown in FIG. 3, catheter 42 may simply enter the bladder and the needle assembly may be positioned facing the target tissue.

In step 206, the needle may pierce the patient's tissue. This may be used in procedures in which the outer layer should not be damaged by ablation. In the example illustrated in FIG. 3, needle 12 may pierce the mucosa 316 of the bladder 302 and access the target tissue 310, e.g., the nerves and/or muscles to be ablated. In such an example, the operator may have determined that the outer layer, mucosa, should not be ablated, but the layer underneath, the submucosa, should be treated with ablation. The present disclosure describes needle assemblies and laser assemblies that may accomplish ablation of a sublayer of tissue, but this disclosure is not limited to needle assemblies described herein. The present disclosure includes methods and devices that may ablate the outer layer of tissue only, and/or sublayers.

Figure 4:
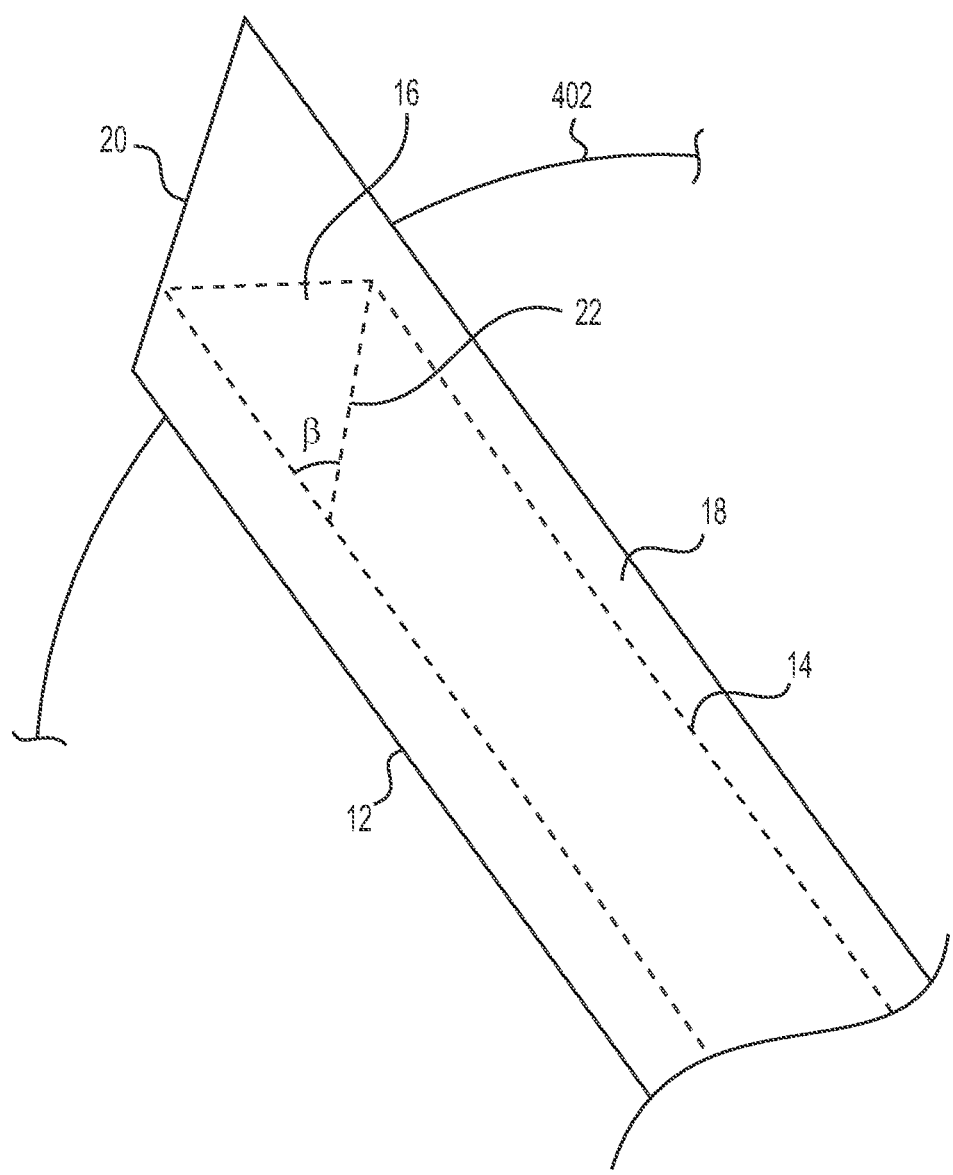
FIG. 4 illustrates an exemplary distal end of the ablation system with a needle piercing the patient's tissue and a prism and laser assembly in a retracted position in accordance with principles of the present disclosure.

In some examples, when the needle pierces the tissue, the laser assembly 35 may be in the retracted position (as shown in FIG. 4). This may allow the needle assembly 11, rather than the prism to pierce the tissue and may protect the laser assembly 35 from damage and/or contamination. FIG. 4 illustrates an example of needle 12 perforating tissue 402 with the laser assembly 35 in the retracted position. The distalmost end of prism 16 is proximal to the distal end 20 of needle 12.

Once the needle pierces the tissue in step 206, method 200 may proceed to step 208. In step 208, a laser fiber disposed within the needle and a prism disposed on a distal end of the laser fiber may slide into the target tissue. For example, laser fiber 14 may be disposed within hollow needle 12 and prism 16 may be disposed on the distal end 22 of needle 14. The laser assembly 35 (e.g., laser fiber 14 along with the attached prism 16) may slide distally into the target tissue (e.g., an extended position). In the extended position, at least a portion of prism 16 (and, in some examples, all of prism 16 and at least a portion of laser fiber 14) may be distal to the distal end 20 of hollow needle 12. FIG. 5A is an exemplary illustration of the laser assembly 35 in the extended position.

Figure 5:
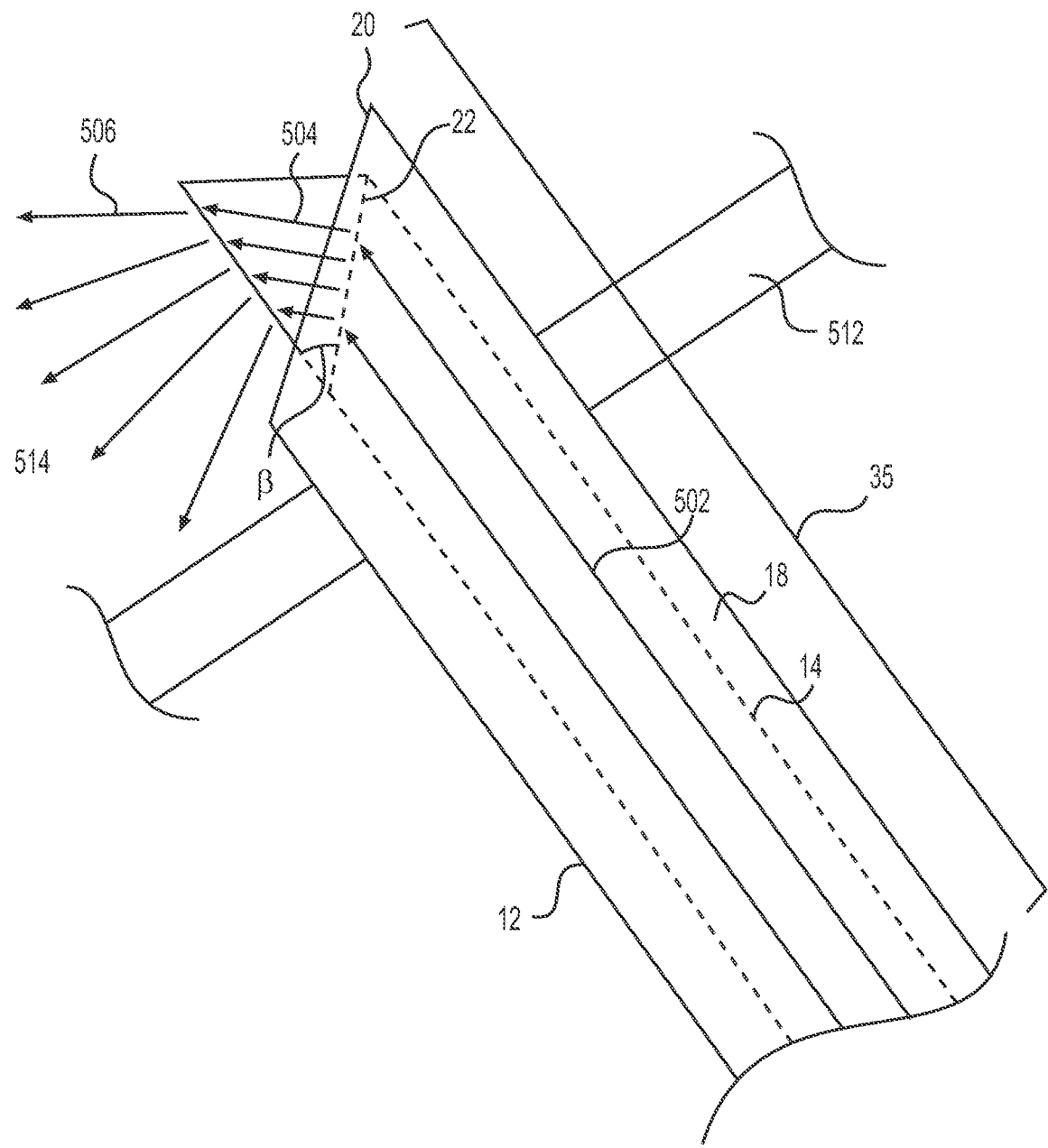
FIG. 5 illustrates an exemplary distal end of the ablation system with the needle piercing the patient's tissue and the prism and laser assembly in an extended position in accordance with principles of the present disclosure.

In step 210, laser energy may be delivered from the laser fiber through the prism and into surrounding tissue. Laser energy may be delivered in any way, including, but not limited it, continuously or paced in intervals (to attenuate effect and avoid tissue necrosis). For example, as illustrated in FIG. 5, laser energy travelling at a first angle 502 (e.g., an angle parallel to the laser fiber) may be delivered from a laser source (e.g., laser source 64) through laser fiber 66, 14. Once the laser energy enters a first face of the prism (e.g., the face that contacts the flat distal end 22 of laser fiber 14), the laser energy may continue in a second direction 504. The laser energy travelling at the second direction 504 may exit a second face of the prism 16 and dissipate the laser energy in a third direction 506 and into target tissue 514. By dissipating the laser energy, the amount of tissue ablated may not be limited to the diameter of the laser fiber 14. This may allow for a smaller incision (e.g., because the laser fiber 14 may be smaller) while ablating a larger area. As noted above, in some examples, prism 16 and/or the entire laser assembly 35 may rotate, thus allowing the dissipated laser energy to ablate (heat) the tissue over a spread of 360 degrees. The second direction 504 and third direction 506 may depend on angle β consistent with the propagation of light through a prism.

Once the target tissue (with or without rotating the prism 16) has been heated the desired amount for the particular type of tissue and/or implementation, the needle and laser fiber may be retracted from the tissue in step 212. In some examples, the laser assembly 35 may be moved into the retracted position (e.g., the distalmost end of the laser assembly 35 is proximal to the distal end 20 of needle 12) before removing the needle assembly from the tissue. In other examples, the laser assembly 35 may remain in the extended position when the needle assembly is removed from the tissue.

In some examples, other tissue may need ablation and/or the operator may desire to ablate other tissue. In the example shown in FIG. 3, ablation may be needed at other locations within the bladder 302 or another location within the urinary tract and the needle assembly 11 and/or the full catheter 42 may be moved to another location of tissue within the bladder 302 and/or urinary tract 300. In other examples, the target tissue may be within the cornea and the second tissue may be located within the patient's second eye. Similarly, the new target tissue may be a different location on the skin, within the digestive tract, within the tumor, and/or within the brain. Once, in examples in which a new target tissue location is desired, the needle assembly and/or catheter is moved, method 200 may return to step 206 and the new target tissue may be pierced by the needle. If a new target tissue location is not desired (for example, all tissue in need of ablation has been ablated), method 200 may proceed to step 216. In step 216, the catheter may be removed from the patient. In the example illustrated in FIG. 3, the catheter 42 may be removed from bladder 302 through the urinary tract 300 and out of patient 310. In examples in which a catheter 42 is not necessary for the desired implementation and/or the needle assembly may access the target tissue by piercing tissue located on the exterior of the patient (e.g., the epidermis, the fat below the surface of the skin, and the cornea of the eye), method 200 may exclude 216.

Figure 6:
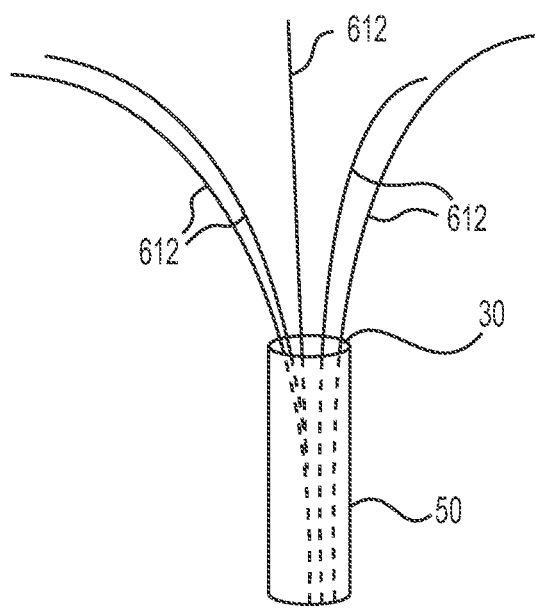
FIG. 6 illustrates an exemplary ablation system with a plurality of needle assemblies in accordance with principles of the present disclosure.
Figure 7:
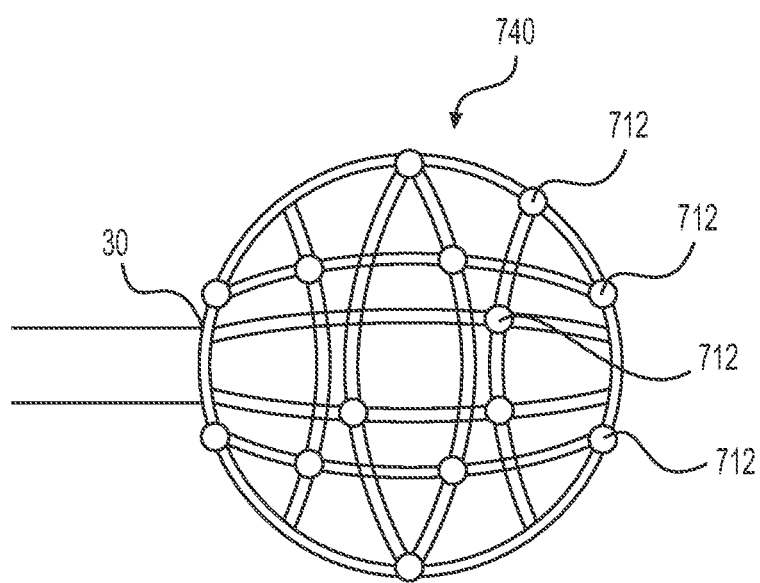
FIG. 7 illustrates an exemplary ablation system with a plurality of needles assemblies disposed on a constellation device in accordance with principles of the present disclosure.

FIGS. 6 and 7 illustrate two examples of alternative distal ends of medical device 50. The distal ends of FIGS. 1, 6, and 7 are merely exemplary and medical device 50, including the distal end, may have any shape and/or configuration. FIG. 6 illustrates medical device 50 with a plurality of needle assemblies 612 cascading out the distal end 30 of medical device 50, each of the plurality of needle assemblies 612 may be similar to needle assembly 11 of FIG. 1. Each of needle assemblies 612 may include a laser fiber disposed within a hollow needle and a prism/prism lens disposed on the distal end of the laser fiber. The needle assemblies 612 may be steered in any way, including those described above with respect to needles assembly 35. Needle assemblies 612 may be sufficiently stiff to perforate the tissue for the desired implementation (e.g., the mucosa for applications within the bladder). Additionally or alternatively, the laser fibers in each of needles 612 may be sufficiently stiff to perforate tissue on their own (e.g., as opposed to needles 612). In a method similar to method 200, the bundle of needles illustrated in FIG. 6 may be steered toward bladder wall and mucosa 310 may be perforated at multiple sites simultaneously. The laser fibers in each of needles 612 may then be used to deliver laser energy to multiple locations of target tissue. In some examples, an outer casing of the laser fibers may serve as a mechanical stopper. For example, the laser fibers may be inserted and pushed into the tissue until the outer casing touches the tissue wall.

In another example, FIG. 7 illustrates an exemplary distal end of medical device 50 with a basket-like constellation device 740 exiting the distal end 30 of catheter 42. The basket-like constellation device 740 of FIG. 7 may include a plurality of needle assemblies 712. The constellation device 740 may be inserted through a lumen of catheter 42 and may transition to an expanded configuration wherein the needle assemblies contact and/or pierce tissue of the patient (e.g., bladder wall of bladder 302). In some implementations, a balloon (not shown) may be inflated within constellation device 740 to expand it. Alternatively, aspects of the constellation device 740 may include memory-shape material, such as nitinol, to transition constellation device 740 to the expanded configuration.

Needle assemblies (e.g., similar to needle assembly 11 of FIG. 1) may be located on or in each leg of constellation device 740. For example, needle assemblies may be disposed within a cavity of a leg and tissue may be suctioned into a cavity to temporarily connect the needle assemblies with the tissue of the patient. Alternatively, the needle assemblies may be extendable from the leg (e.g., radially outward of the leg). In some examples, the needle assemblies may also be retractable.

In some examples, the needle assemblies may be capable of delivering a drug (e.g., Botox, lidocaine, antimuscarinic, other neurotoxins, local anesthetics, anti-inflammatories, a beta adrenergic agonists, etc.) and/or hydrogels to the tissue of the patient. For example, the needle inner diameter may be approximately ten percent wider than the outer diameter of the laser fiber (e.g., a larger space 18 between needle 12 and laser fiber 14). Once the sharp end 20 of needle 12 pierces the tissue, a drug and/or hydrogel may be delivered to the target tissue as an additional or alternative treatment to ablation.

In some examples, laser assembly 35 may be excluded from the system. Instead, any device that may emit laser energy laterally relative to the longitudinal axis of needle 12 may be disposed within needle 12. For example, a conventional side-firing laser may be disposed within hollow needle 12 in place of laser assembly 35. A laser fiber may include a tip portion with a reflective material. For example, a reflective material disposed at or near the distal end of the laser fiber may be at an approximately 45 degree angle to the longitudinal axis of the laser fiber. Such a configuration would ablate the tissue approximately 90 degrees from the longitudinal axis of the laser fiber. Unlike the configurations of FIG. 5, however, a conventional side-firing laser may have an ablation area limited to the diameter of the laser fiber, because without prism 16, the laser energy introduced by the laser fiber would not have dissipated/diverged prior to entering the tissue.

In another example, instead of dissipating/diverging the laser energy as shown in FIG. 5, the system disclosed herein may narrow or focus the laser energy. For example, a lens (not shown) may be attached to the distal end 22 of laser fiber 14. A convex lens or gradient-index lens may focus the laser energy emitted from laser fiber 14. Either the distalmost end of the lens or the distalmost end of a prism attached to the distal end of the lens may include an angled, reflective surface to achieve side-firing. In one example, the lens may receive laser energy from laser fiber 14. The laser energy emitted from the laser fiber 14 may enter the convex or gradient-index lens and, consistent with the propagation of light through such a convex or gradient-index lens, the laser energy may converge. The laser energy may then reflect off the reflective distalmost end of the lens or the prism. The laser energy may be reflected by the angled distalmost end of the prism or lens and a narrowed, focused laser energy may be emitted into target tissue. In some examples, the angled distalmost end may additionally or alternatively be a separate fabrication.

In some examples, it may be desired to ablate a greater area surrounding the laser fiber. For example, 360 degrees of ablation may be desired. As described above, the laser fiber may be rotated to achieve such a result. Additionally or alternatively, multiple laser fibers may be disposed within the needle. For example, four fibers may be positioned with prisms facing as to dissipate light into 4 different directions at an approximately 90 degree angle from one another. Further, in an example in which the distalmost end is reflective, the end of the fiber could be multifaceted to reflect light in a radial pattern, and thus eliminating the need for rotation.

In addition, aspects of the aforementioned embodiments may be combined with any other aspects of any other embodiments, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the disclosure being indicated by the following claims.

What is claimed is:

1. A method for ablating target tissue comprising:
   aligning a needle of a medical device with the target tissue;
   piercing tissue adjacent to the target tissue with the needle;
   distally sliding a laser fiber that is moveably disposed within the needle such that a distal end of the laser fiber is aligned with a distal end of the needle, wherein the needle is hollow and the laser fiber includes a prism;
   retracting the needle proximally to allow the laser fiber to extend distally beyond the needle; and
   delivering laser energy through the laser fiber and prism, wherein the laser energy is delivered distally beyond the distal end of the needle.

2. The method of claim 1, further comprising:
   inserting a catheter into the patient, wherein the needle is disposed within a lumen of the catheter.

3. The method of claim 1, wherein the target tissue is within a bladder of the patient.

4. The method of claim 3, wherein the pierced tissue is part of mucosa and the target tissue is part of submucosa.

5. The method of claim 1, further comprising:
   rotating the laser fiber.

6. The method of claim 1, further comprising:
   introducing at least one of a fluid or a gel into the target tissue through a space between the needle and the laser fiber.

7. A method for ablating target tissue comprising:
   aligning a needle of a medical device with the target tissue;
   piercing tissue adjacent to the target tissue with the needle;
   sliding distally a laser fiber that is moveably disposed within the needle such that the distal end of the laser fiber is aligned with a distal end of the needle, wherein the needle is hollow and the laser fiber includes a prism at a distal end;
   retracting the needle proximally in order to expose a portion of the laser fiber or the prism distally beyond a distal end of the needle;
   delivering laser energy through the laser fiber and prism; and
   introducing at least one of a fluid or a gel into the target tissue through a space between the needle and the laser fiber.

8. The method of claim 7, wherein the step of retracting the needle proximally includes exposing the distal end of the laser fiber distally beyond the distal end of the needle such that the exposed portion of the laser fiber or the prism extends through an open distal end of the needle.

9. The method of claim 7, further including inserting a catheter into the patient, wherein the needle is disposed within a lumen of the catheter.

10. The method of claim 7, wherein the target tissue is within a bladder of the patient.

11. The method of claim 7, wherein the pierced tissue is part of mucosa and the target tissue is part of submucosa.

12. The method of claim 7, further comprising:
    rotating the laser fiber.

* * * * *